United States Patent
Ely et al.

(10) Patent No.: US 11,960,035 B2
(45) Date of Patent: Apr. 16, 2024

(54) METHODS AND SYSTEMS FOR ENCODING AND DECODING RADIO FREQUENCY DATA

(71) Applicant: KONINKLIJKE PHILIPS N.V., Eindhoven (NL)

(72) Inventors: Gregory Tsiang Ely, Somerville, MA (US); Faik Can Meral, Mansfield, MA (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 346 days.

(21) Appl. No.: 17/606,914

(22) PCT Filed: Apr. 30, 2020

(86) PCT No.: PCT/EP2020/062159
§ 371 (c)(1),
(2) Date: Oct. 27, 2021

(87) PCT Pub. No.: WO2020/225135
PCT Pub. Date: Nov. 12, 2020

(65) Prior Publication Data
US 2022/0206129 A1 Jun. 30, 2022

Related U.S. Application Data

(60) Provisional application No. 62/843,766, filed on May 6, 2019.

(51) Int. Cl.
*G01S 7/52* (2006.01)
*G01N 29/26* (2006.01)
*G01S 15/89* (2006.01)

(52) U.S. Cl.
CPC ........ *G01S 7/52034* (2013.01); *G01N 29/262* (2013.01); *G01S 7/52026* (2013.01);
(Continued)

(58) Field of Classification Search
CPC ............ G01S 7/52034; G01S 7/52026; G01S 7/5208; G01S 15/8927; G01N 29/262;
(Continued)

(56) References Cited

U.S. PATENT DOCUMENTS 6,013,032 A 1/2000 Savord
2008/0294050 A1 11/2008 Shinomura et al.
(Continued)

FOREIGN PATENT DOCUMENTS

JP 2007215766 A 8/2007

OTHER PUBLICATIONS

Besson Adrien et al: "Compressive Multiplexing of Ultrasound Signals", 2018 IEEE International Ultrasonics Symposium (IUS), IEEE, Oct. 22, 2018 (Oct. 22, 2018), pp. 1-4, XP033480183 (Year: 2018).*

(Continued)

*Primary Examiner* — Santiago Garcia

(57) ABSTRACT

Systems and methods for encoding radiofrequency, RF, data, e.g., electrical signals, by a microbeamformer are disclosed herein. The microbeamformer may use a pseudo-random sampling pattern (700) to sum samples of the RF data stored in a plurality of memory cells. The memory cells may be included in a delay line of the microbeamformer in some examples. The summed samples may form an encoded signal transmitted to a decoder which reconstructs the original RF data from the encoded signal. The decoder may use knowledge of the pseudo-random sampling pattern to reconstruct the original data in some examples.

20 Claims, 13 Drawing Sheets

(52) U.S. Cl.
CPC ........ *G01S 7/5208* (2013.01); *G01S 15/8927* (2013.01); *G01N 2291/044* (2013.01); *G01N 2291/106* (2013.01)

(58) Field of Classification Search
CPC ....... G01N 2291/044; G01N 2291/106; G01N 29/0609; G01N 29/0645; A61B 8/5207
See application file for complete search history.

(56) References Cited

U.S. PATENT DOCUMENTS

| | | | |
|---|---|---|---|
| 2011/0021921 A1 | 1/2011 | Tsao | |
| 2014/0046188 A1* | 2/2014 | Yen | A61B 8/4427 600/447 |
| 2014/0157084 A1* | 6/2014 | Shalvi | G06F 11/1068 714/768 |
| 2015/0035576 A1* | 2/2015 | Romano | H03K 5/135 327/262 |
| 2021/0270950 A1* | 9/2021 | Passi | G01S 7/524 |
| 2021/0275149 A1* | 9/2021 | Bottenus | A61B 8/4488 |
| 2022/0133269 A1* | 5/2022 | Xu | H10N 39/00 600/438 |

OTHER PUBLICATIONS

Besson et al: "Compressive Multiplexing of Ultrasound Signals"; IEEE International Ultrasonics Symposium, 2018.
Cohen et al: "Sparse Convolutional Beamforming for Ultrasound Imaging"; arXiv:1805.05101v2, Aug. 3, 2018, pp. 1-18.
Dony"Karhunen-Loeve Transform", The Transform and Data Compression Handbook, Ed. K.R. Rao and P.C. Yip, Boca Raton, CRC Press LLC, 2001.
Halvorsrod et al: "A Discrete Time U Beamformer for CMUT Arrays—Behaviorial Simulati"; ONS Using Systemc; IEEE 2005, p. 500-5-3.
PCT/EP2020/062159 ISR & Written Opinion, dated Jul. 29, 2020.
Lok et al: "Real-Time Channel Data Compression for Improved Software Beamforming Using Micro-Beamforming With Error Compensation"; IEEE, 2015.
Siritan et al: "Enhanced Pseudo-Dynamic Receive Beamforming Using Focusing Delay Error Compensation"; IEEE 2014 Biomedical Engineering International Conference.
Tarantola: "Inverse Problem Theory and Methods for Model Parameter Estimation"; Society for Industrial and Applied Mathematics, 2005.

* cited by examiner

METHODS AND SYSTEMS FOR ENCODING AND DECODING RADIO FREQUENCY DATA

CROSS-REFERENCE TO PRIOR APPLICATIONS

This application is the U.S. National Phase application under 35 U.S.C. § 371 of International Application No. PCT/EP2020/062159, filed on Apr. 30, 2020, which claims the benefit of U.S. Provisional Patent Application No. 62/843,766, filed on May 6, 2019. These applications are hereby incorporated by reference herein.

TECHNICAL FIELD

This application relates to encoding and decoding radio frequency data associated with ultrasound signals. More specifically, this application relates to encoding radio frequency data with a microbeamformer for decoding by an ultrasound imaging system.

BACKGROUND

While offering high resolution, ultrasound image acquisition with focused beam transmissions and dynamic receive beamforming poses a time limit to the real time volumetric imaging. Compared to unfocused beam imaging methods, it takes about an order of magnitude longer for focused beam transmissions to cover a three-dimensional (3D) imaging region-of-interest (ROI), which results in a much slower frame rate. This can be a serious problem for imaging applications where high frame rate is important such as 3D cardiac imaging. For faster imaging, unfocused ultrasound transmissions may be used. Unfocused transmissions may illuminate a much larger portion of the ROI with a single transmission compared to focused beam transmissions. These unfocused transmissions may consist of plane waves or spherically or cylindrically diverging waves.

Ultrasound probes with two-dimensional (2D) transducer arrays may be used for faster and/or higher resolution 3D imaging. However, 2D transducer arrays may have an array of hundreds or thousands of transducer elements which need to be coupled to the imaging system. To avoid a large number of wires between an ultrasound probe and the imaging system base, some ultrasound probes include microbeamformers. A microbeamformer receives signals from the individual transducer elements and performs some preliminary beamforming operations to combine signals from groups of transducer elements (e.g., sub-arrays, patches) into an output signal. The preliminary beamforming operations may include applying delays to the signals from the individual transducer elements and then summing the delayed signals to generate the output signal. The number of output signals may be based on the number of patches the transducer array is divided into. Combining the signals of groups of individual transducer elements into output signals may reduce the number of channels required. For example, an ultrasound probe may have 128 output channels coupled to the ultrasound system base. However microbeamformers are typically designed for focused transmit beams and image quality may start to degrade when the receive beam is steered away from the transmit beam main axis. Implementing diverging and plane wave imaging with transducer arrays coupled to microbeamformers may degrade image contrast and introduces grating-lobe artifacts. A technique for combining the potential high speed 3D imaging capabilities of diverging and plane wave imaging with transducer arrays including microbeamformers with reduced image degradation is desired.

SUMMARY

Methods and systems for microbeamforming operations that may increase image acquisition speed and quality are disclosed. The microbeamforming and beamforming operations perform encoding and decoding. Instead of constructing an image directly from microbeamformed data, the original data is reconstructed based on a limited number of measurements and image formation is performed based on the reconstruction. A jitter sampling scheme may be used by the microbeamformer to encode data in a manner that is compatible with analog RAM. The microbeamformer encoding may multiplex spatial frequencies over fast time. Based on the output of the coded microbeamformer, the original signal may be reconstructed with a computationally inexpensive inversion method as described herein. An image may be formed from the reconstructed data.

According to examples of the present disclosure, a system may include a transducer array including a plurality of transducer elements. The transducer elements may be configured to receive ultrasound echoes and convert the ultrasound echoes into electrical signals (e.g., RF data, RF signals). The system may include a microbeamformer coupled to the plurality of transducer elements. The microbeamformer may include a first delay line coupled to a first transducer element of the plurality of transducer elements. The first delay line may include a first plurality of memory cells configured to store the electrical signals received from the first transducer element. The microbeamformer may further include a second delay line coupled to a second transducer element of the plurality of transducer elements. The second delay line may include a second plurality of memory cells configured to store the electrical signals received from the second transducer element. The microbeamformer may be configured to jitter sample the electrical signal stored in the first plurality of memory cells and the second plurality of memory cells and generate a jitter signal. The system may include a decoder configured to receive the jitter signal and generate a reconstructed signal representative of the electrical signals.

According to examples of the present disclosure, a method may include acquiring a plurality of samples of an electrical signal, wherein the electrical signal is associated with an acoustic signal, storing the plurality of samples in a plurality of memory cells, wherein individual memory cells of the plurality of memory cells store individual samples of the plurality of samples, pseudo-randomly selecting a subset of the plurality of memory cells, wherein the subset includes fewer than the plurality of memory cells, summing the individual samples of the plurality of samples stored in the subset of the plurality of memory cells to generate a jitter signal, and decoding the jitter signal to generate a reconstructed signal.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

According to the principles of the present disclosure, rather than using a traditional delay-and-sum approach to combine signals from individual transducer elements, a microbeamformer can be used as an encoder to encode radio frequency (RF) data associated with received echoes and the encoded data may be transmitted from an ultrasound probe to an imaging system base where the encoded data is decoded to reconstruct the original RF data (e.g., signal). An image may then be generated based on the reconstructed data. An image generated from the reconstructed data may have fewer artifacts (e.g., grating lobes) compared to images generated from typical delay-and-sum beamforming. In addition to mitigating the artifacts of microbeamforming, the reconstruction of the original data may allow for more advanced adaptive beamforming algorithms that may require the original channel data.

RF data may be highly correlated and/or compressible (e.g., in fast time) in ultrasound imaging applications. Encoding the RF data may exploit this redundancy and compress the original RF data. However, despite the compression, the original RF data may still be recoverable by decoding the encoded data. This may reduce the amount of data required to be transmitted between the ultrasound probe and the imaging system base.

Figure 1:
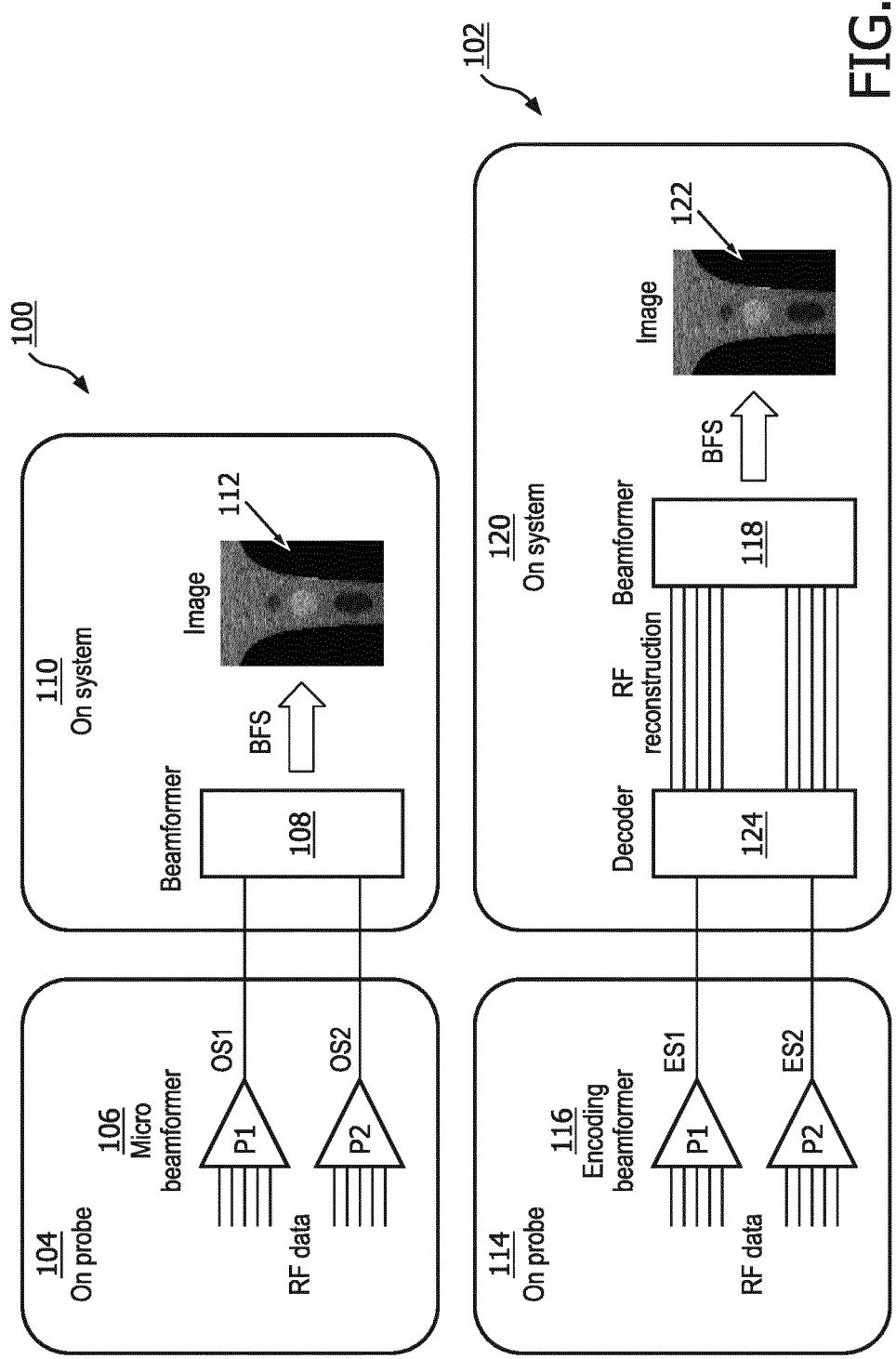
FIG. 1 shows simplified diagrams illustrating an imaging system with a typical microbeamformer arrangement and an imaging system with a microbeamformer arrangement in accordance with examples of the present disclosure.

FIG. 1 shows simplified diagrams illustrating an imaging system 100 with a typical microbeamformer arrangement and an imaging system 102 with a microbeamformer arrangement in accordance with examples of the present disclosure. Imaging system 100 includes an ultrasound probe 104, which may include a transducer array with individual transducer elements (not shown). The transducer array may transmit ultrasound signals and receive echo signals responsive to the transmitted ultrasound signals. The transducer elements may generate electrical signals (e.g., RF data) responsive to the echo signals. The RF data may be transmitted from the transducer elements to a microbeamformer 106. The microbeamformer may divide the signals from transducer elements into patches. In the example shown in FIG. 1, the transducer elements are grouped into two patches P1, P2. The microbeamformer may apply appropriate delays to the signals received from each transducer in a patch and sum the delayed signals into a single output signal OS1, OS2 for each patch P1, P2, respectively. The appropriate delay may be determined, at least in part, on a relative location of a transducer element to other transducer elements in the patch. The output signals OS1 and OS2 may be partially beamformed signals. The output signals OS1 and OS2 may be provided to a main beamformer 108 included in a system base 110 of the imaging system 100. The main beamformer 108 may apply additional delays to the output signals OS1 and OS2 to form a fully beamformed signal BFS used to generate an ultrasound image 112.

Imaging system 102 may include ultrasound probe 114, which may include a transducer array with individual transducer elements (not shown), that transmit RF data to a microbeamformer 116 that divides the transducer elements into patches P1, P2, similar to system 100. In contrast to system 100, microbeamformer may sample the RF data received from the transducer elements and/or apply delays in a pseudo-random manner then sum the delayed samples of each patch to generate encoded signals ES1, ES2. The encoded signals ES1, ES2 may be provided to a decoder 124 located on a system base 120. The decoder 124 may reconstruct the original RF data from the encoded signals ES1, ES2. The reconstructed data may be provided to a beamformer 118, which may perform beamforming operations to generate image 122.

According to examples of the present disclosure, a system may include a transducer array including a plurality of transducer elements. The transducer elements may be configured to receive ultrasound echoes and convert the ultrasound echoes into electrical signals (e.g., RF data, RF signals). The system may include a microbeamformer coupled to the plurality of transducer elements. The microbeamformer may include a first delay line coupled to a first transducer element of the plurality of transducer elements. The first delay line may include a first plurality of memory cells configured to store the electrical signals received from the first transducer element. The microbeamformer may further include a second delay line coupled to a second transducer element of the plurality of transducer elements. The second delay line may include a second plurality of memory cells configured to store the electrical signals received from the second transducer element. In some examples, the delay lines may be programmable delay lines. In some examples, the plurality of memory cells are configured as a circular buffer. The microbeamformer may be configured to jitter sample the electrical signal stored in the first plurality of memory cells and the second plurality of memory cells and generate a jitter signal. The system may include a decoder configured to receive the jitter signal and generate a reconstructed signal representative of the electrical signals.

In some examples, the system may include a main beamformer configured to generated a beamformed signal based at least in part on the reconstructed signal. In some examples, the main beamformer may include the decoder. In some examples, the system may include a transmit controller, wherein the transmit controller provides delays to be added to the jitter signal by the microbeamformer to focus or steer a beam associated with the ultrasound echoes.

In some examples, the microbeamformer is configured to generate the jitter signal by pseudo-randomly summing the electrical signals sampled from the first plurality of memory cells and the second plurality of memory cells. In some examples, the decoder is configured to apply a covariance matrix to the jitter signal to generate the reconstructed signal, wherein the covariance matrix is based, at least in part, on the jitter sample of the electrical signal stored in the first and second pluralities of memory cells.

In some examples, the microbeamformer is configured to jitter sample the electrical signal stored in the first and second pluralities of memory cells using a pseudo-random pattern of time sample segments. In some examples, the pseudo-random pattern of time sample segments is configured such that individual memory cells of the first plurality of memory cells and the second plurality of memory cells are sampled no more than once per memory cycle.

In some examples, a first subset of the plurality of transducer elements are grouped into a first patch including the first transducer element and a second subset of the plurality of transducer elements are grouped into a second patch including the second transducer element.

Figure 2:
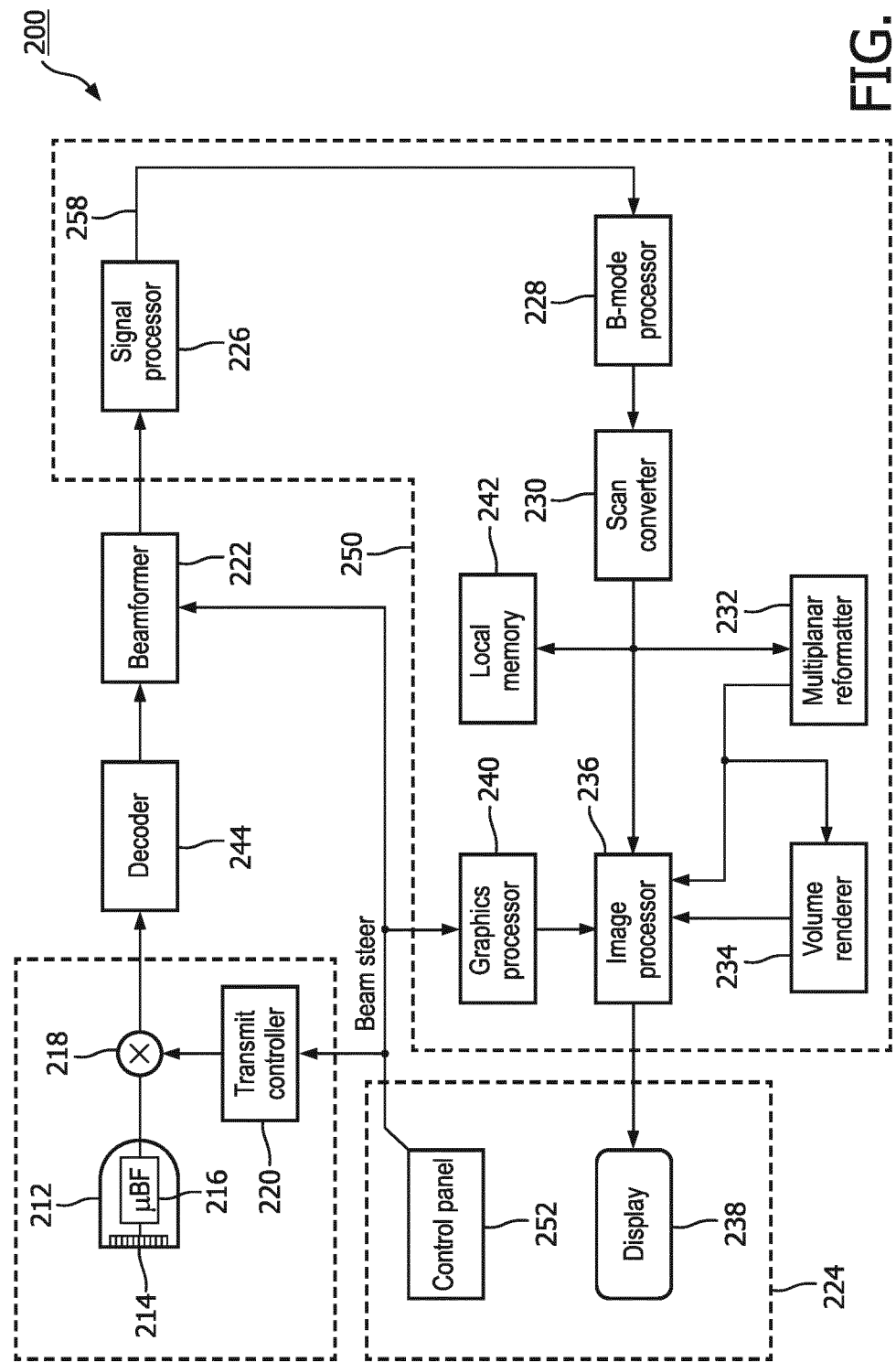
FIG. 2 is a block diagram of an ultrasound imaging system arranged in accordance with some examples of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an intravascular ultrasound (IVUS) catheter probe. In other embodiments, the transducer array 214 may be in the form of a flexible array configured to be conformally applied to a surface of subject to be imaged (e.g., patient). The transducer array 214 is configured to transmit ultrasound signals (e.g., beams, waves) and receive echoes responsive to the ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

The transducer array 214 may be coupled to a microbeamformer 216, which may be located in the ultrasound probe 212, and which may control the transmission and reception of signals by the transducer elements in the array 214. In some embodiments, the microbeamformer 216 may control the transmission and reception of signals by active elements in the array 214 (e.g., an active subset of elements of the array that define the active aperture at any given time). The transducer elements in the array 214 may generate radio frequency (RF) data (e.g., electrical signals) and transmit the RF data to the microbeamformer 216.

In some embodiments, the microbeamformer 216 may be coupled, e.g., by a probe cable or wirelessly, to a transmit/receive (T/R) switch 218, which switches between transmission and reception and protects a decoder 244 and main beamformer 222 from high energy transmit signals. In some embodiments, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 214 under control of the microbeamformer 216 is directed by the transmit controller 220, which may be coupled to the T/R switch 218 and a decoder 244 coupled to a main beamformer 222. The transmit controller 220 may control the direction in which beams are steered. Beams may be steered straight ahead from (orthogonal to) the transducer array 214, or at different angles for a wider field of view. Unfocused beams (e.g., plane waves, diverging waves) may also be transmitted. The transmit controller 220 may also be coupled to a user interface 224 and receive input from the user's operation of a user control. The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices.

According to the principles of the present disclosure, the microbeamformer 216 may receive the RF data from the transducer elements of the transducer array 214 to generate an encoded signal. Details of the encoding will be explained in more detail further below. The microbeamformer 216 may be coupled to the decoder 244 by a probe cable or wirelessly. The encoded signal may be provided by the microbeamformer 216 to the decoder 244. The decoder 244 may decode the encoded signal provided by the microbeamformer 216 to reconstruct the RF data. The reconstructed RF data may be provided by the decoder 244 to the main beamformer 222. In some embodiments, the decoder 244 may be implemented by one or more processors.

The main beamformer 222 may perform beamforming operations (e.g., delay-and-sum or other beamforming operations) to generate a fully beamformed signal. The beamformed signals of beamformer 222 are coupled to processing circuitry 250, which may include one or more processors (e.g., a signal processor 226, a B-mode processor 228).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

The B-mode processor can employ amplitude detection for the imaging of structures in the body. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. The multiplanar reformatter 232 can convert echoes which are received from points in a common plane in a volumetric region of the body into an ultrasonic image (e.g., a B-mode image) of that plane, for example as described in U.S. Pat. No. 6,443,896 (Detmer). The scan converter 230 and multiplanar reformatter 232 may be implemented as one or more processors in some embodiments.

A volume renderer 234 may generate an image (also referred to as a projection, render, or rendering) of the 3D dataset as viewed from a given reference point, e.g., as described in U.S. Pat. No. 6,530,885 (Entrekin et al.). The volume renderer 234 may be implemented as one or more processors in some embodiments. The volume renderer 234 may generate a render, such as a positive render or a negative render, by any known or future known technique such as surface rendering and maximum intensity rendering.

Output (e.g., B-mode images) from the scan converter 230, the multiplanar reformatter 232, and/or the volume renderer 234 may be coupled to an image processor 236 for further enhancement, buffering and temporary storage before being displayed on an image display 238. A graphics processor 240 may generate graphic overlays for display with the images. These graphic overlays can contain, e.g., standard identifying information such as patient name, date and time of the image, imaging parameters, and the like. For these purposes the graphics processor may be configured to receive input from the user interface 224, such as a typed patient name or other annotations. The user interface 224 can also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including B-mode images, executable instructions, inputs provided by a user via the user interface 224, or any other information necessary for the operation of the system 200.

As mentioned previously system 200 includes user interface 224. User interface 224 may include display 238 and control panel 252. The display 238 may include a display device implemented using a variety of known display technologies, such as LCD, LED, OLED, or plasma display technology. In some embodiments, display 238 may comprise multiple displays. The control panel 252 may be configured to receive user inputs (e.g., threshold value, filter type, render type). The control panel 252 may include one or more hard controls (e.g., buttons, knobs, dials, encoders, mouse, trackball or others). In some embodiments, the control panel 252 may additionally or alternatively include soft controls (e.g., GUI control elements or simply, GUI controls) provided on a touch sensitive display. In some embodiments, display 238 may be a touch sensitive display that includes one or more soft controls of the control panel 252.

In some embodiments, various components shown in FIG. 2 may be combined. For instance, image processor 236 and graphics processor 240 may be implemented as a single processor. In another example, the scan converter 230 and multiplanar reformatter 232 may be implemented as a single processor. In some embodiments, various components shown in FIG. 2 may be implemented as separate components. In some embodiments, one or more of the various processors shown in FIG. 2 may be implemented by general purpose processors and/or microprocessors configured to perform the specified tasks. In some embodiments, one or more of the various processors may be implemented as application specific circuits. In some embodiments, one or more of the various processors (e.g., image processor 236) may be implemented with one or more graphical processing units (GPU).

Figure 3:
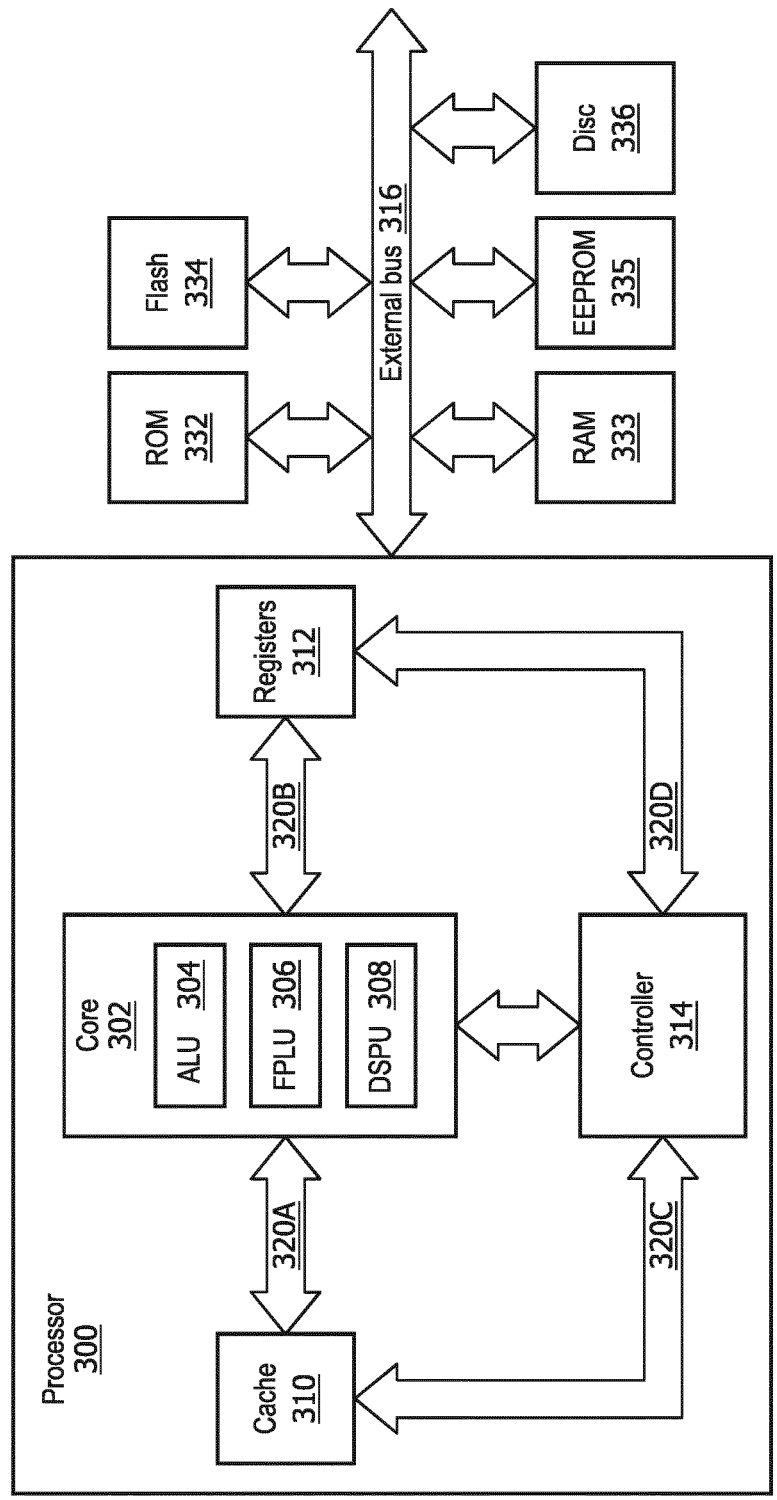
FIG. 3 is a block diagram illustrating an example processor in accordance with some examples of the present disclosure.

FIG. 3 is a block diagram illustrating an example processor 300 according to principles of the present disclosure. Processor 300 may be used to implement one or more processors described herein, for example, image processor 236 shown in FIG. 2. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 304. In some embodiments, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some embodiments the registers 312 may be implemented using static memory. The register may provide data, instructions and addresses to the core 302.

In some embodiments, processor 300 may include one or more levels of cache memory 310 communicatively coupled to the core 302. The cache memory 310 may provide computer-readable instructions to the core 302 for execution. The cache memory 310 may provide data for processing by the core 302. In some embodiments, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 2) and/or outputs from the processor 300 to other processors and/or components included in the system (e.g., display 238 and volume renderer 234 shown in FIG. 2). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache memory 310 may communicate with controller 314 and core 302 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache 310, and/or register 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RAM, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some embodiments, the external memories may be included in a system, such as ultrasound imaging system 200 shown in FIG. 2, for example local memory 242.

Figure 4:
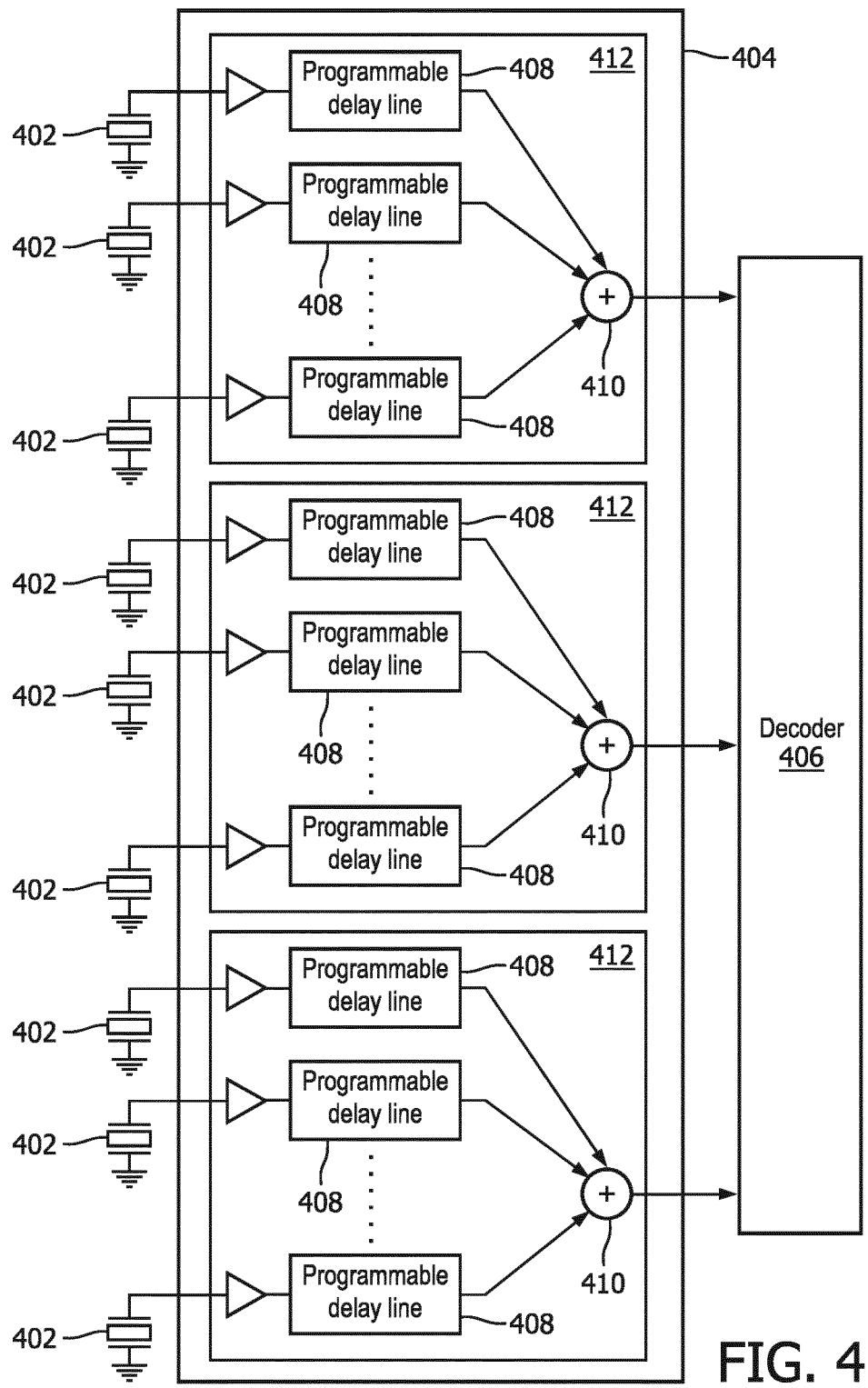
FIG. 4 is a block diagram of components of an imaging system in accordance with examples of the present disclosure.

As previously discussed with reference to FIG. 1, a transducer array including multiple transducer elements may be divided into patches, sometimes also referred to as subarrays or simply groups, by the microbeamformer. FIG. 4 is a block diagram of components of an imaging system 400 in accordance with examples of the present disclosure. The imaging system 400 may include transducer elements 402, a microbeamformer 404, and a decoder 406. The transducer elements 402 may be included in a transducer array in an ultrasound probe (not shown in FIG. 4). The transducer elements 402 may provide RF signals to respective delay lines 408 of the microbeamformer 404. In some examples, such as the one shown in FIG. 4, the delay lines 408 may be programmable delay lines. The delay lines 408 may be coupled to summing nodes 410. All of the delay lines coupled to a same summing node 410 may be included in a same patch 412. Outputs from the summing nodes 410 of each patch 412 may be provided to the decoder 406. The components of imaging system 400 may be used to implement one or more of the components of imaging system 200 shown in FIG. 2. For example, microbeamformer 404 may be used to implement microbeamformer 216 in FIG. 2.

Figure 5:
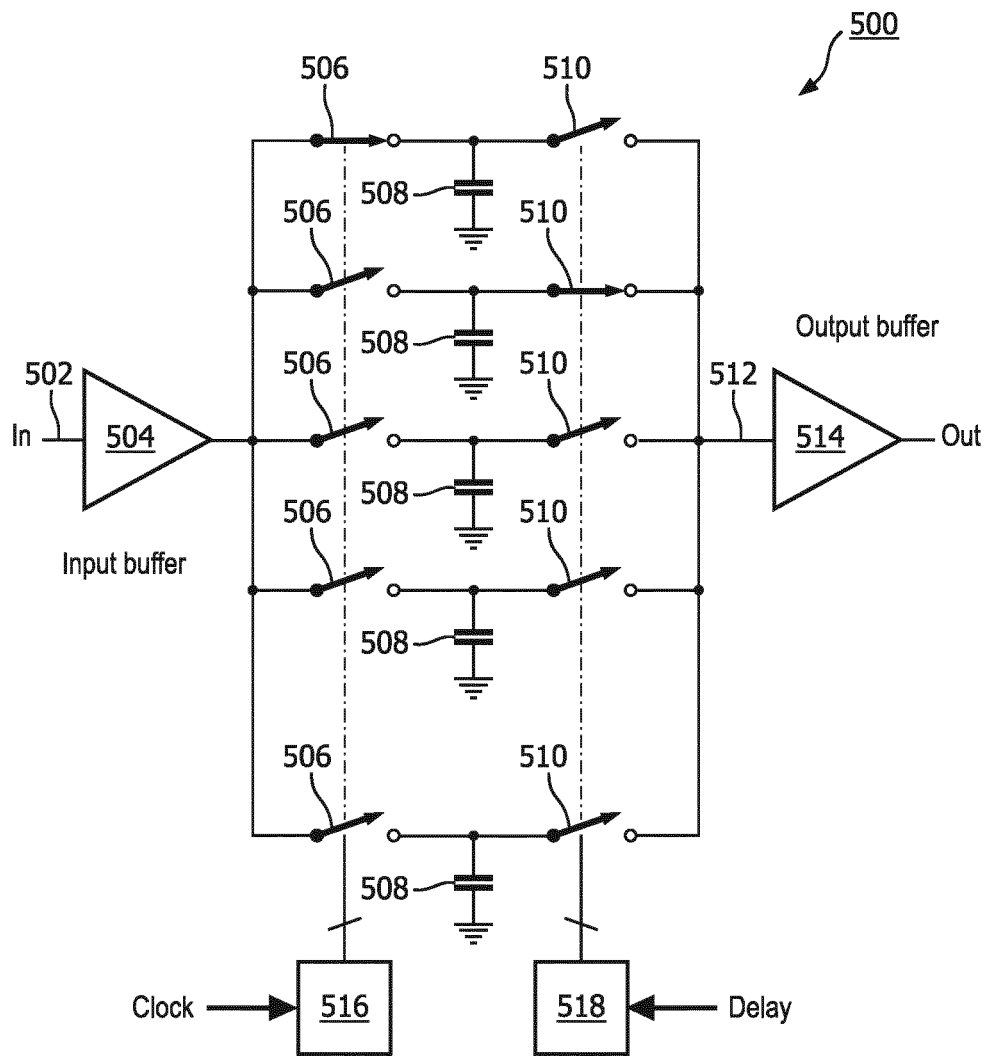
FIG. 5 is a block diagram of a programmable delay line in accordance with examples of the present disclosure.

FIG. 5 is a block diagram of a programmable delay line 500 in accordance with examples of the present disclosure. In some examples, programmable delay line 500 may be used to implement delay line 408 in FIG. 4. The delay line 500 may receive an input via input line 502. In some examples, such as the one shown in FIG. 5, the input line 502 may include an input buffer 504. The input line 502 may receive an electrical signal (e.g., RF data) from a transducer element (not shown in FIG. 5), for example, transducer element 402 shown in FIG. 4. The delay line 500 may include a number of input switches 506. The input switches 506 may direct electrical signals from the input line 502 to one or more memory cells 508 by selectively coupling the memory cells 508 to the input line 502. The memory cells 508 may be implemented with capacitors in some examples, such as the one shown in FIG. 5. The memory cells 508 may store the electrical signals received from the input line 502. The delay line 500 may include a number of output switches 510. The output switches 510 may selectively couple one or more memory cells 508 to an output line 512. When coupled to the output line 512, the electrical signals stored in the memory cells 508 may be transmitted to the output line 512. The output line 512 may transmit the electrical signal to a summing node (not shown in FIG. 5) such as summing node 410 shown in FIG. 4. In some examples, such as the one shown in FIG. 5, the output line 512 may include an output buffer 514.

The operation of the input switches 506 may be controlled by an input controller logic circuit 516. The input controller logic circuit 516 may receive a clock signal and change which input switches 506 are closed responsive to a rising and/or falling clock edges in the clock signal. In some examples, the input controller logic circuit 516 may include a counter and a multiplexer. The input controller logic circuit 516 controls which memory cells 508 store an electrical signal received via the input line 502 each clock cycle. Thus, the delay line 500 effectively samples the electrical signal on the input line 502 and stores the samples in the memory cells 508. The sampling rate may be based on a frequency of the clock signal. The sampling rate of the delay line 500 should be no less than a Nyquist rate of the electrical signal to avoid aliasing the electrical signal.

In some examples, the delay line 500 may be configured as a circular buffer. That is, each clock cycle, one input switch 506 is closed to couple one memory cell 508 to the input line 502 to store the electrical signal present on the input line 502 during that clock cycle. The input controller logic circuit 516 cycles through the input switches 506 in a same order. For example, a first memory cell 508 (e.g., the top memory cell 508 shown in FIG. 5) may hold a first time sample, a second memory cell 508 may hold a second time sample, etc. After all of the memory cells 508 have been written to, the input controller logic circuit 516 may repeat the cycle, overwriting any stored data in the memory cells 508 during a next memory cycle. For example, if the delay line 500 includes eight input switches 506 and eight memory cells 508, after eight clock cycles, data in the first memory cell 508 will be rewritten with new data received from the input line 502.

The operation of output switches 510 may be controlled by an output controller logic circuit 518. The output controller logic circuit 518 may receive delay data and change which output switches 510 are closed to couple memory cells 508 to the output line 512. The delay data may be received from one or more shift registers (not shown) or a transmit controller (not shown in FIG. 5), such as transmit controller 220 in FIG. 2. In other examples, the delay data may be programmed into a memory included in the output controller logic circuit 516. The time between when a sample of the electrical signal is stored on the memory cell 508 and when the memory cell 508 is coupled to the output line 512 may determine the delay of the electrical signal. Providing the sample of the electrical signal to the output line 512 may be a destructive read. That is, once the memory cell 508 has provided the sample to the output line 512, the memory cell 508 no longer stores the electrical signal. Thus, a sample can only be read from a memory cell 508 once. Once read, there is no valid data in the memory cell 508 until the memory cell 508 is again coupled to the input line 502 to receive a new sample of the electrical signal.

The delay line 500 shown in FIG. 5 is provided for exemplary purposes, and principles of the present disclosure are not limited to the delay line shown in FIG. 5. Examples of other suitable delay lines and/or delay line controls that may be used may be found in U.S. Pat. Nos. 5,997,479 and 6,013,032 to Savord and U.S. Pat. No. 8,161,817 to Robinson, which are incorporated herein by reference for any purpose.

In a typical microbeamformer operation, each sample from each memory cell 508 may be appropriately delayed by control of the output switches 510 and provided to the output line 512 for summing with the outputs of other delay lines of the patch. When the delay line 500 is arranged as a circular buffer, the maximum delay may be limited to the length of a memory cycle (e.g., eight cycles in the example described previously). Otherwise, a sample may be overwritten by a newly acquired sample. The summed outputs of the delay lines of the patch may then be provided by the microbeamformer to a main beamformer.

According to principles of the present disclosure, a jitter sampling scheme may be used to control the output switches 510. The jitter sampling scheme, as will be described in more detail with reference to FIGS. 6-9, may apply pseudo-random delays to the electrical signals stored in the memory cells 508. Furthermore, not all samples acquired by the memory cells 508 may be provided to the output line 512. That is, the jitter sampling scheme may down-sample the electrical signal. The jitter sampling scheme may be provided to the output controller logic circuit 518 to control the operation of the output switches 510 to perform the jitter sampling operation. The jitter sampling scheme may encode the electrical signal such that the electrical signal may be reconstructed by a decoder.

Figure 6:
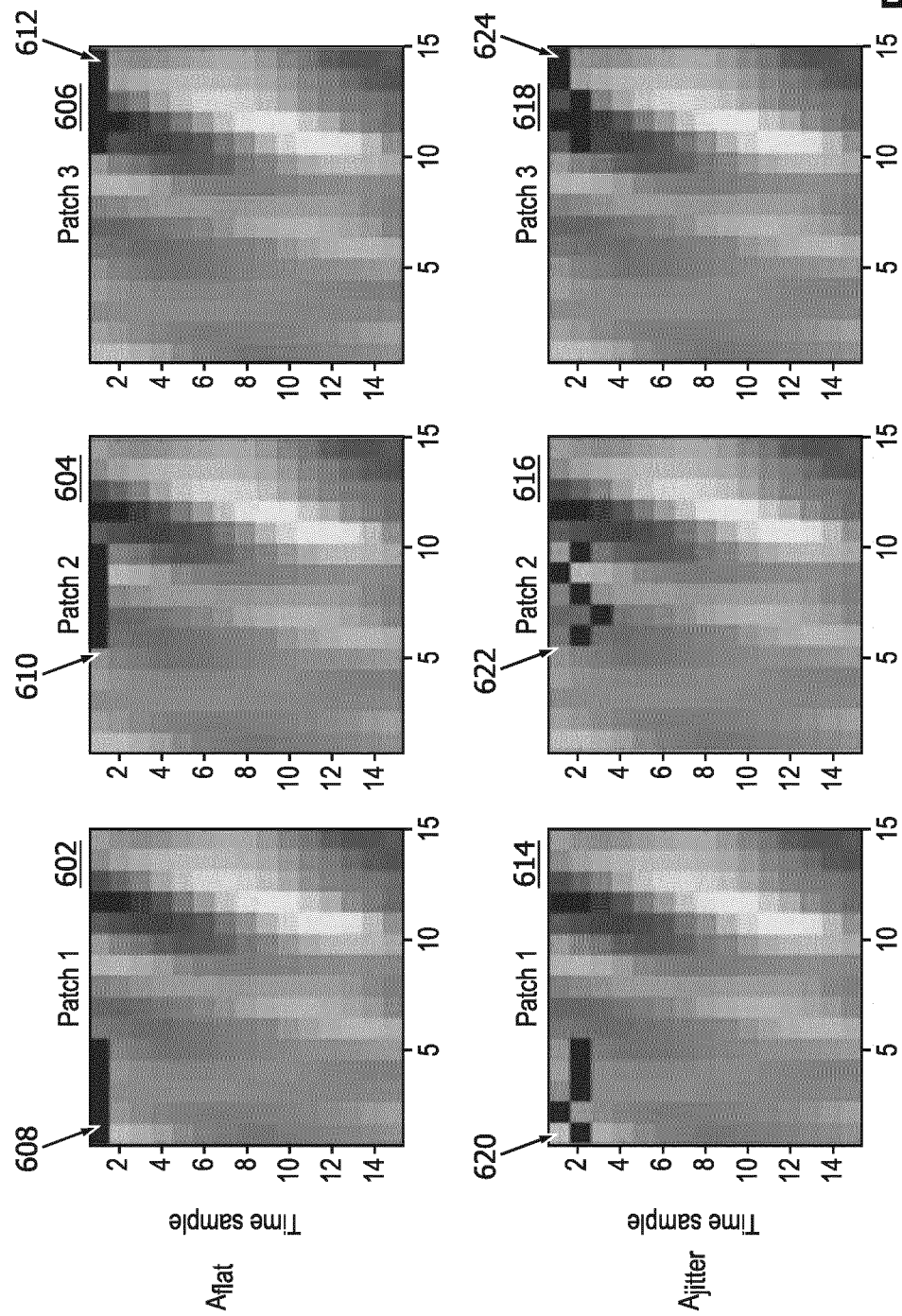
FIG. 6 a graphical illustration of typical delay-and-sum beamforming and jitter sampling in accordance with examples of the present disclosure.

FIG. 6 is a graphical illustration of typical delay-and-sum (DAS) beamforming ($A_{flat}$) and jitter sampling ($A_{jitter}$) in accordance with examples of the present disclosure. For ease of understanding, the jitter sampling scheme is first described in reference to a one-dimensional array having fifteen transducer elements grouped into three patches, where each patch includes five transducer elements. In DAS beamforming, samples of electrical signals (e.g., RF data) from transducer elements acquired by delay lines (e.g., delay line 500) are delayed such that signals from the same spatial location are aligned in time (e.g., delayed) and then summed. This is shown in panels 602, 604, and 606. The horizontal axis corresponds to the transducer element and the vertical axis corresponds to the time sample for that transducer element. The time samples may be stored in memory cells, such as memory cells 508. As indicated by the dark blue squares 608 for Patch 1, dark blue squares 610 for Patch 2, and dark blue squares 612 for patch 3, the first time sample from each transducer element are summed together after alignment to obtain the signals for Patch 1, Patch 2, and Patch 3. For example, the first time samples may be stored in the top memory cell 508 shown in FIG. 5. Next, the second time samples for each transducer element may be aligned and summed. For example, the second time samples may be stored in a memory cell 508 below the top memory cell 508 shown in FIG. 5. This process may continue for every time sample acquired by the delay lines. The signals from five transducer elements from each patch are combined and sent by the microbeamformer to the imaging system base as a single signal. Thus, in the example shown in FIG. 5, three rather than fifteen signals are sent to the imaging system base from the ultrasound probe.

In accordance with principles of the present disclosure, the microbeamformer may be used to encode the electrical signal rather than perform typical DAS beamforming. The encoding may use a jitter sampling scheme that pseudo-randomly sums time samples stored in the delay lines for the transducer elements. An example of a jitter sampling scheme is illustrated panels 614, 616, and 618. As shown by the dark blue squares 620, Patch 1 combines the second time samples for transducer elements 1, 3, 4, and 5 and the first time sample from transducer element 2. As shown by dark blue squares 622, Patch 2 combines the second time sample of transducer elements 6, 8, 10, the third time sample of transducer element 7 and the first time sample of transducer element 9. As shown by dark blue squares 624, Patch 3 combines the second time sample of transducer elements 11 and 13 and the first time samples of 12, 14, and 15.

The jitter sampling scheme may reduce the amount of data transferred from ultrasound probe to the imaging system base, but may allow the original fully sampled data to be reconstructed. The jitter sampling scheme may access only a few previous samples (e.g., three in the example shown in FIG. 6), so delay lines with large numbers of memory cells are not required. The jitter sampling scheme reads each memory cell only once per memory cycle. Furthermore, as seen in FIG. 6, the jitter sampling scheme communicates across patches by varying the pseudo-random pattern across patches as well as time.

Figure 7:
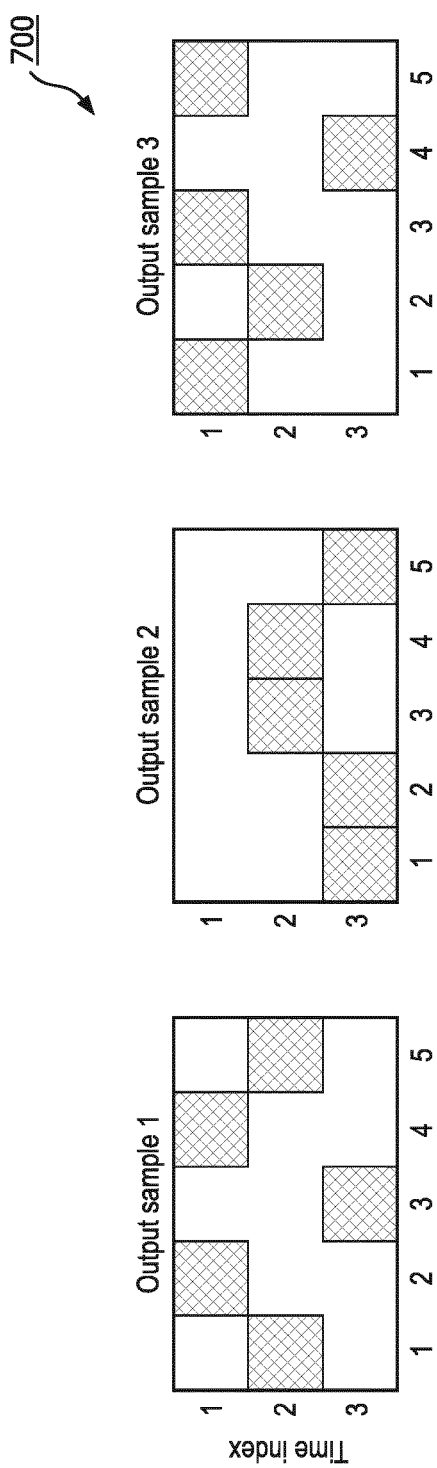
FIG. 7 is an illustration of an example jitter sample grouping in accordance with examples of the present disclosure

FIG. 7 illustrates an example jitter sample grouping 700 in accordance with examples of the present disclosure. The example jitter sample grouping 700 shows how the jitter sampling scheme may vary across time. Each panel 702, 704, and 706 shows a non-overlapping delay grouping for the jitter sampling scheme that is used to generate three sequential output samples from a patch. The light-colored blocks of each panel 702, 704, and 706 illustrate the time sample for each transducer element read from a memory cell. In the example jitter sampling scheme shown in FIG. 7, three sequential sample patterns are grouped together and then randomly summed across the transduce elements such that each memory cell is read once. Unlike conventional microbeamforming shown in the top panels of FIG. 6, the delays are not monotonically increasing. While FIG. 7 shows three groups that sample a segment of fifteen samples, other numbers may be used. For example, five different sets of time samples groups such that the data is divided into twenty-five time sample segments may be used. In this example, the jitter sampling scheme is repeated periodically for each non-overlapping fifteen sample segment. Other jitter sampling schemes of non-overlapping sampling could also be used.

Heuristically, the jitter sampling acquisition scheme for encoding the RF signal (e.g., electrical signals) by the microbeamformer can be understood as follows: while two consecutive fast time samples of a microbeamformer are very similar and sample identical spatial frequencies (e.g., a first time sample stored in a first memory cell and a sequential second time sample stored in a second memory cell of a delay line), two consecutive jitter samples sample different spatial frequencies. In a sense, the jitter sampling acquisition is multiplexing different spatial frequencies over fast time. This is possible if the microbeamformer clock (e.g., the clock signal controlling the input control logic circuit 516 that controls the operation of the input switches 506 in FIG. 5) is significantly faster than the RF signal sampling requirement. However, jitter sampling may perform better compression compared to simply down-sampling the data to its Nyquist limit.

Both $A_{flat}$ and $A_{jitter}$ shown in FIG. 6 can be written as linear operators acting to down sample the original data (x) consisting of 225 data points (15 time samples×3 patches×5 transducer elements per patch) to a reduced number of measurements (y) (15 time samples×3 patch output signals).

$$A_{flat}x=y \text{ or } A_{jitter}x=y$$

In the one dimensional example of FIGS. 6 and 7 of microbeamforming the data compression rate is 20% for both $A_{flat}$ and $A_{fitter}$.

Figure 8:
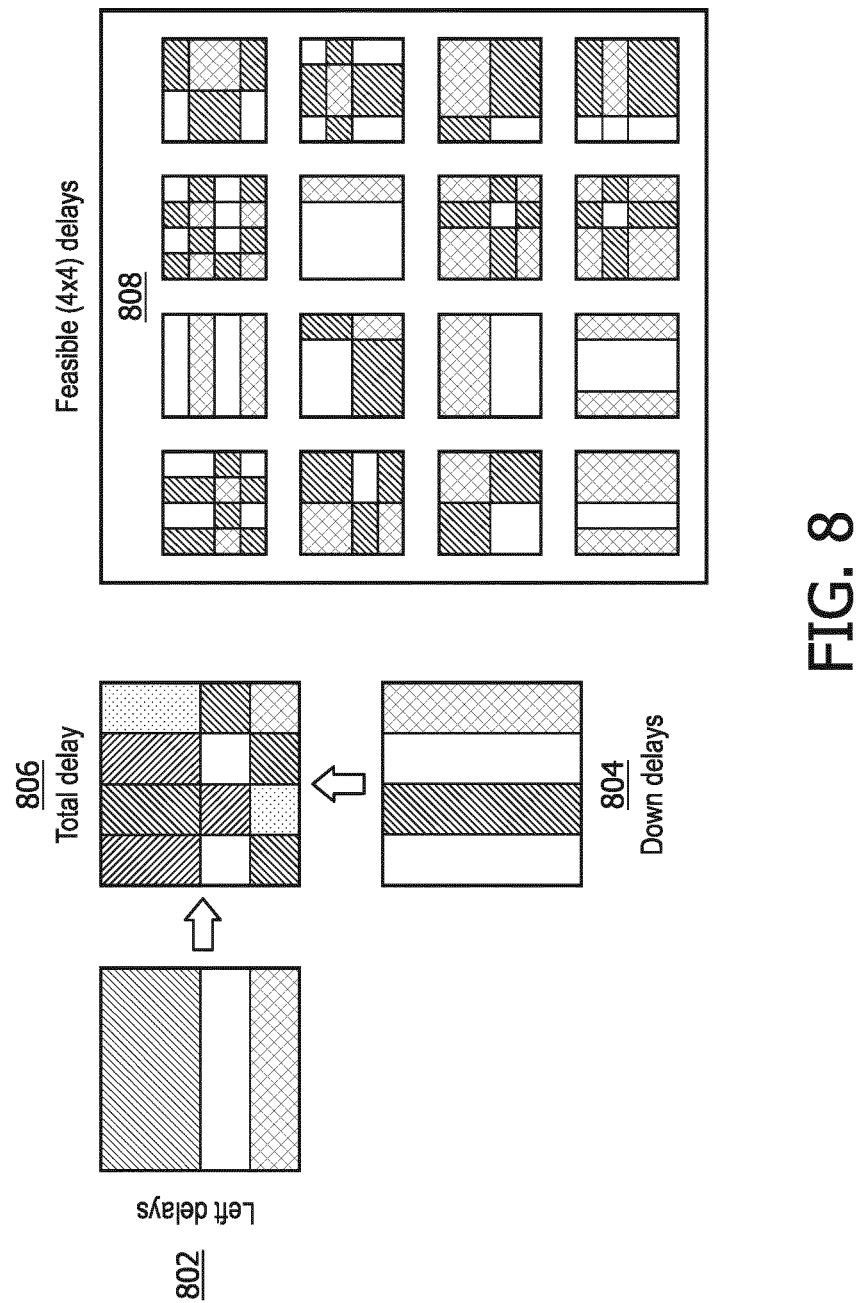
FIG. 8 is an illustration of delays across transducer elements in a two dimensional array in accordance with examples of the present disclosure

The jitter sampling scheme may be extended to two-dimensional (2D) transducer arrays. In 2D, the microbeamformer groups the transducer elements in rectangular patches (e.g., 3×3, 4×4, 5×5). Depending on the type of microbeamformer included in an ultrasound probe, the microbeamformer may impose additional constraints to the delays which can be applied to the transducer elements of each patch. Each patch may be controlled by row-wise and column-wise constant delays (e.g., left-delays and down-delays). The row-wise 802 and column-wise delays 804 are shown in FIG. 8. In the example shown in FIG. 8, transducer elements are grouped as 4×4 patches. The delay applied to the electrical signals of each individual transducer element may be the sum of these row-wise delays 802 and column-wises delays 804. The control line values for left and down delays may be used to generate a pseudo-random delay pattern of the patch 806. As shown in FIG. 8, different colors indicate different delay values fed to the delay lines and resulting delays of transducer elements in the patch 806. Pane 808 of FIG. 8 shows examples of several pseudo random delay patterns which satisfy the microbeamformer control constraint that can be used to implement jitter sampling scheme. Similar to the 1D case shown in FIGS. 6-7, three sequential time samples may be grouped together and then randomly summed. Again memory cells are read only once, so the method is not dependent on samples that were destroyed in prior reads.

Figures 9A, 9B:
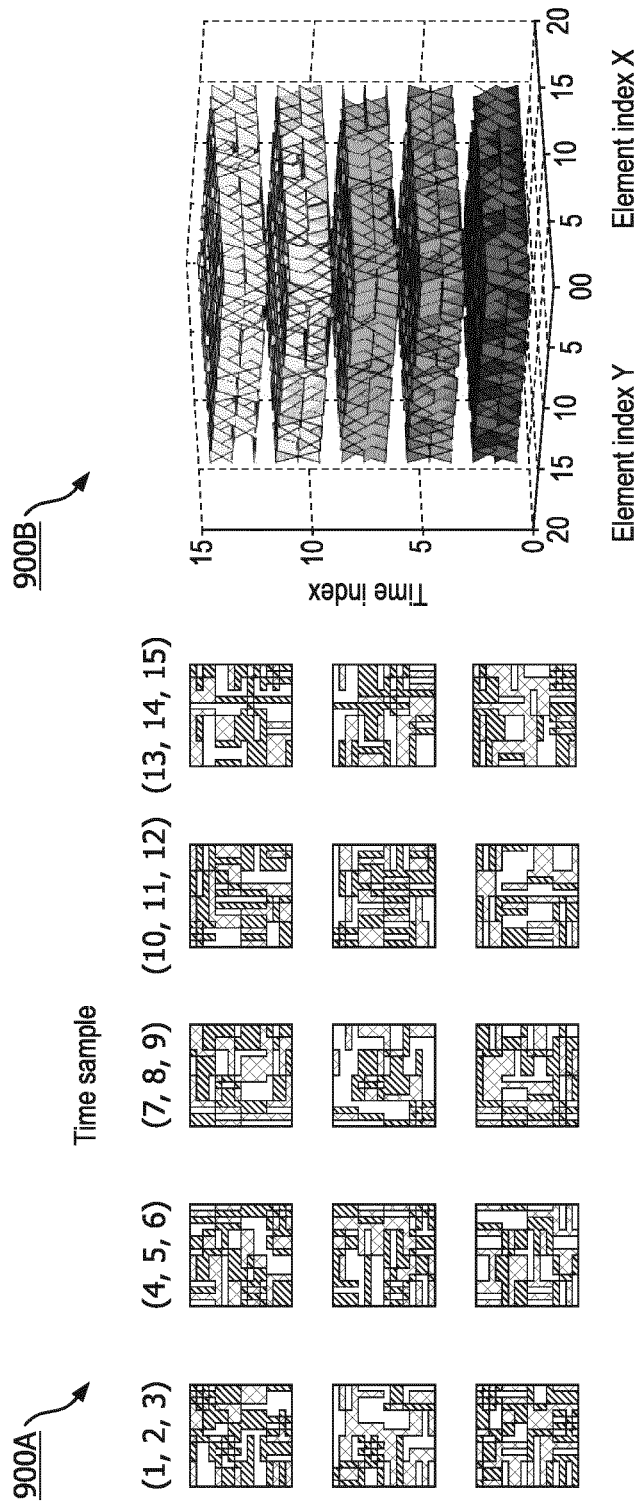
FIG. 9A is an illustration of an example of a set of pseudo-random delay patterns over the 16-element-by-16-element array with 4-by-4 patches in accordance with examples of the present disclosure.
FIG. 9B is an illustration of example grouping 900B with three sequential time samples is shown in three dimensions in accordance with examples of the present disclosure.

In some examples five different sets of time sample groups may be used such that the data is divided into fifteen time sample segments. For a simulated 2D array consisting of 256 elements (16×16), an example of a set of pseudo-random delay patterns 900A over the sixteen 4-element-by-4-element patches corresponding to these fifteen time sample segments are shown in FIG. 9A. An example grouping 900B with three sequential time samples is shown in three dimensions is shown in FIG. 9B. FIGS. 9A and 9B illustrate that the samples may be grouped into non-overlapping sets of three similar to the one-dimensional array acquisition scheme shown in FIGS. 6-7.

The jitter samples are collected by the microbeamformer and combined to generate a jitter signal. The jitter signal may be the encoded RF data sampled from the transducer elements. In some examples, delays may be added to the jitter samples and/or jitter signal for focusing or steering of ultrasound beams. The jitter signal may then be provided to a decoder for reconstruction of the RF data (e.g., original RF data).

The reconstruction of the RF data from the encoded signal (e.g., jitter signal) may be an inverse problem. In reconstructing an estimate of the original (e.g. true) data (x), the compressibility and non-randomness of the RF data may be leveraged to improve reconstructions. To reconstruct the RF data, it may be assumed that the RF data is drawn from a Gaussian distribution with some covariance matrix $\Sigma$ and an estimate of x ($x_{map}$) may be found given the observed data (y) and the prior assumption on the distribution of x, p(x).

This estimate of x ($x_{map}$) is known as the maximum a posterior (MAP) estimator as it maximizes the posterior distribution, $$\max_x p(x|y) \propto p(y|x)p(x) \quad (1)$$

Where p(y|x) is the probability of a measurement y given true data x. For a linear operator A, such as $A_{jitter}$, the MAP estimator has a closed form solution, $$x_{map} = \Sigma A_{jitter}^t (A_{jitter} \Sigma A_{jitter}^t)^{-1} y \quad (2)$$

Where $\Sigma$ is the estimated covariance matrix and y is the output the microbeamformer (e.g., jitter signal). The decoder may have the pseudo-random pattern ($A_{jitter}$) used by the microbeamformer to generate the jitter signal. Thus, Equation (2) may be used to reconstruct the original data and perform beamforming. The covariance matrix $\Sigma$ may be estimated from a single frame of data in some examples and/or from synthetically generated data. The matrix in Equation (2) can be pre computed such that the inversion only requires a single matrix multiplication and may be extremely fast.

Since both the signal reconstruction and beamforming operations are linear, they could be combined in a single operation that reconstructs the final image from the jitter data. That is, the decoder could be included in a main beamformer (or vice versa) in some examples.

Figure 10:
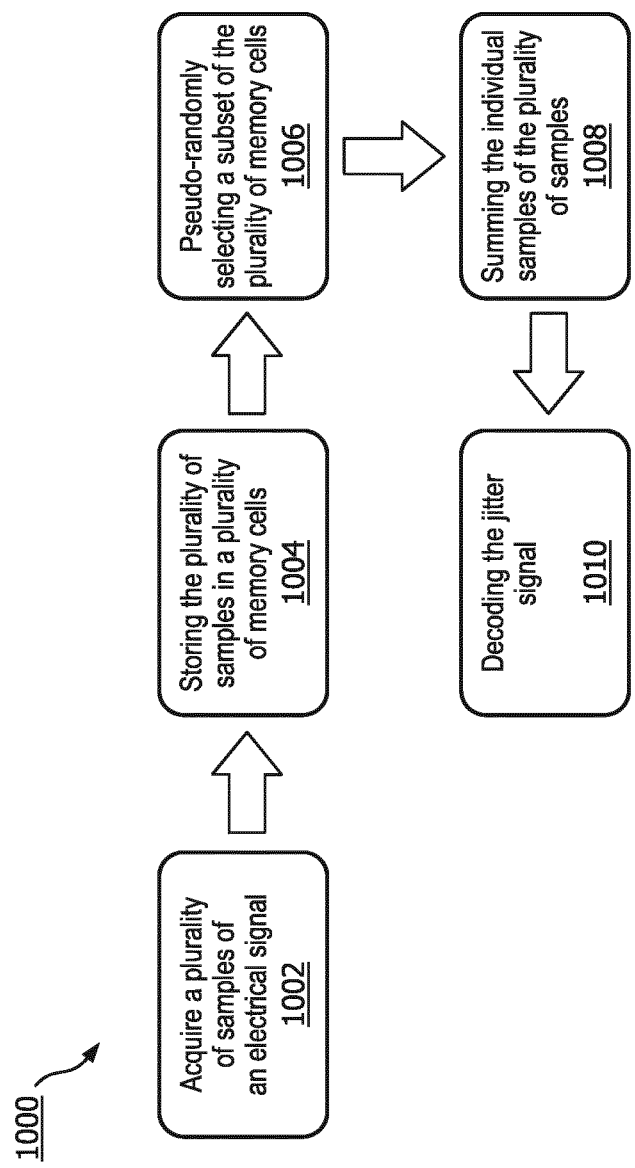
FIG. 10 is a flow chart of a method in accordance with some examples of the present disclosure.

FIG. 10 is a flow chart of a method 1000 in accordance with examples of the present disclosure. The flow chart summarizes a microbeamforming encoding method described herein. At block 1002, a step of "acquiring a plurality of samples of an electrical signal" may be performed. In some examples, acquiring the plurality of samples of the electrical signal is controlled by a clock signal. A frequency of the clock signal may be higher than a Nyquist rate of the electrical signal.

The electrical signal may be associated with an acoustic signal. For example, the electrical signal may be generated by transducer elements responsive to echoes received. The echoes may be responsive to ultrasound signals transmitted by the transducer elements and/or other transducer elements. The electrical signal may be radio frequency data (e.g., radio frequency signal). For example, prior to block 1002, the step of "transmitting an ultrasound signal" may be performed. The transmitting may be performed by a transducer array comprising a plurality of transducer elements in some examples. The ultrasound signal may be a plane wave or a diverging wave in some examples. After transmitting the ultrasound signal, a step of "receiving the acoustic signal responsive to the ultrasound signal," may be performed. The acoustic signal (e.g., echoes) may be received with the transducer array. After receiving the acoustic signal, a step of "generating the electrical signal responsive to the acoustic signal" may be performed. The electrical signal may be generated with the plurality of transducer elements in some examples. In some examples, at least one of the plurality of memory cells is coupled to individual ones of the plurality of transducer elements. In some examples, the plurality of transducer elements are grouped into a plurality of patches and summing the individual samples of the plurality of samples comprises summing individual samples associated with at least two of the plurality of patches.

At block 1004, a step of "storing the plurality of samples in a plurality of memory cells" may be performed. The individual memory cells of the plurality of memory cells may store individual samples of the plurality of samples.

At block 1006, a step of "pseudo-randomly selecting a subset of the plurality of memory cells" may be performed. The subset may include fewer than the plurality of memory cells. In some examples, pseudo-randomly selecting the subset of the plurality of memory cells may down-sample the electrical signal. In some examples, after block 1006, a step of "adding delays to the pseudo-randomly selecting the subset of the plurality of memory cells" may be performed. The delays may focus or steer a beam associated with the acoustic signal.

At block 1008, a step of "summing the individual samples of the plurality of samples" may be performed. The individual samples may be stored in the subset of the plurality of memory cells. The summing of the individual samples may generate a jitter signal.

At block 1010, a step of "decoding the jitter signal" may be performed. Decoding the jitter signal may generate a reconstructed signal. Decoding may include applying the matrix described in Equation (2) to the jitter signal. In some examples, the covariance matrix may be based at least in part on the pseudo-randomly selecting.

Figure 11:
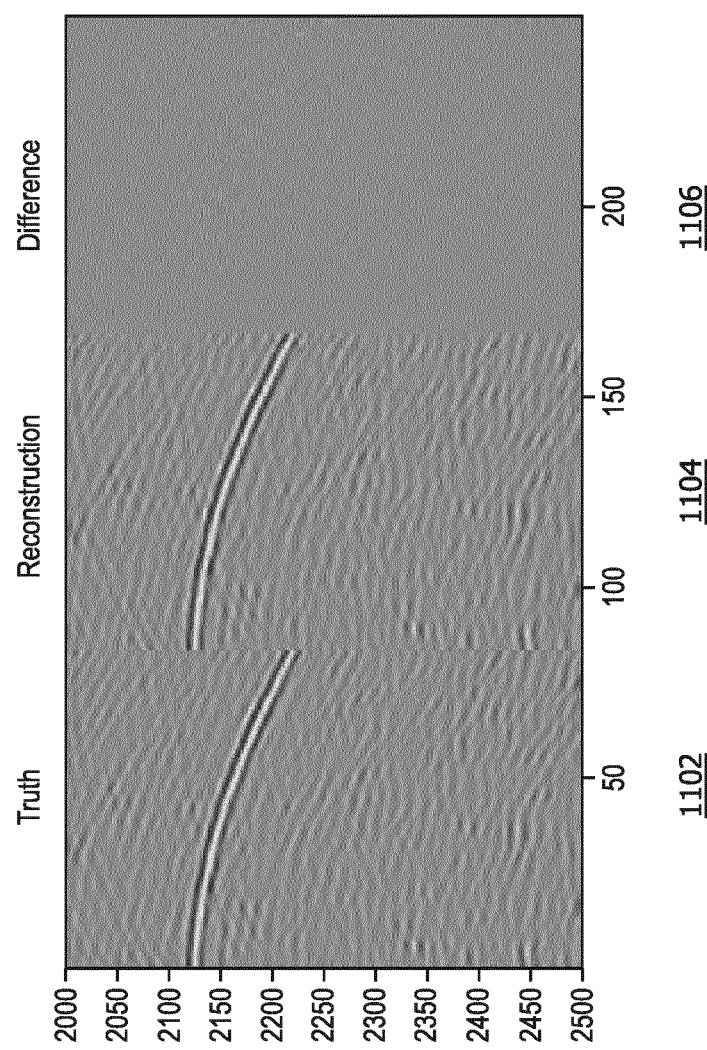
FIG. 11, FIG. 12 and FIG. 13 show examples of original signals and reconstructed signals generated in accordance with the examples of the present disclosure.
Figure 12:
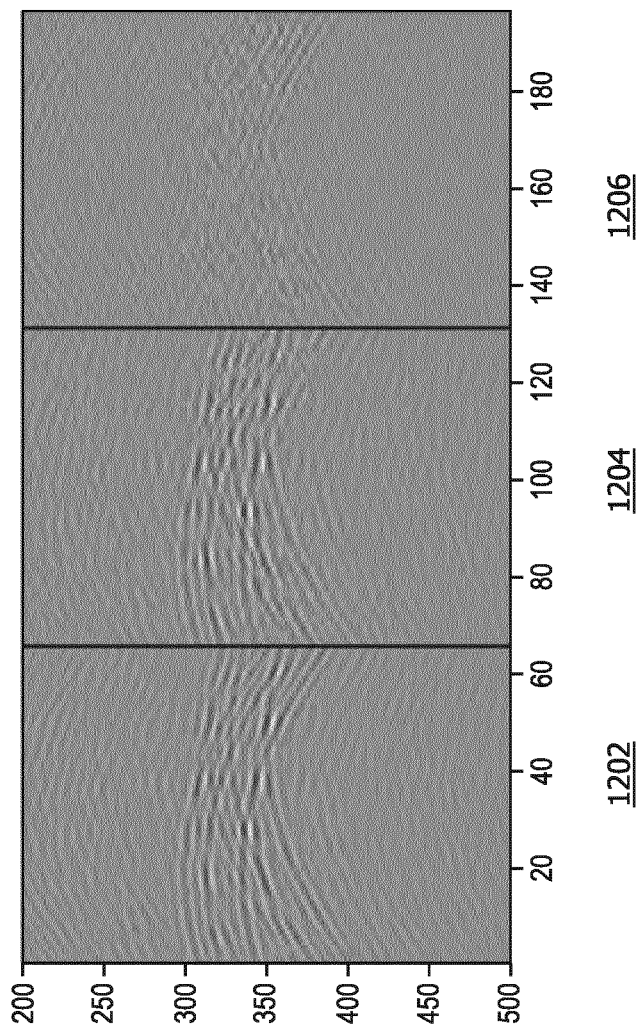
Figure 13:
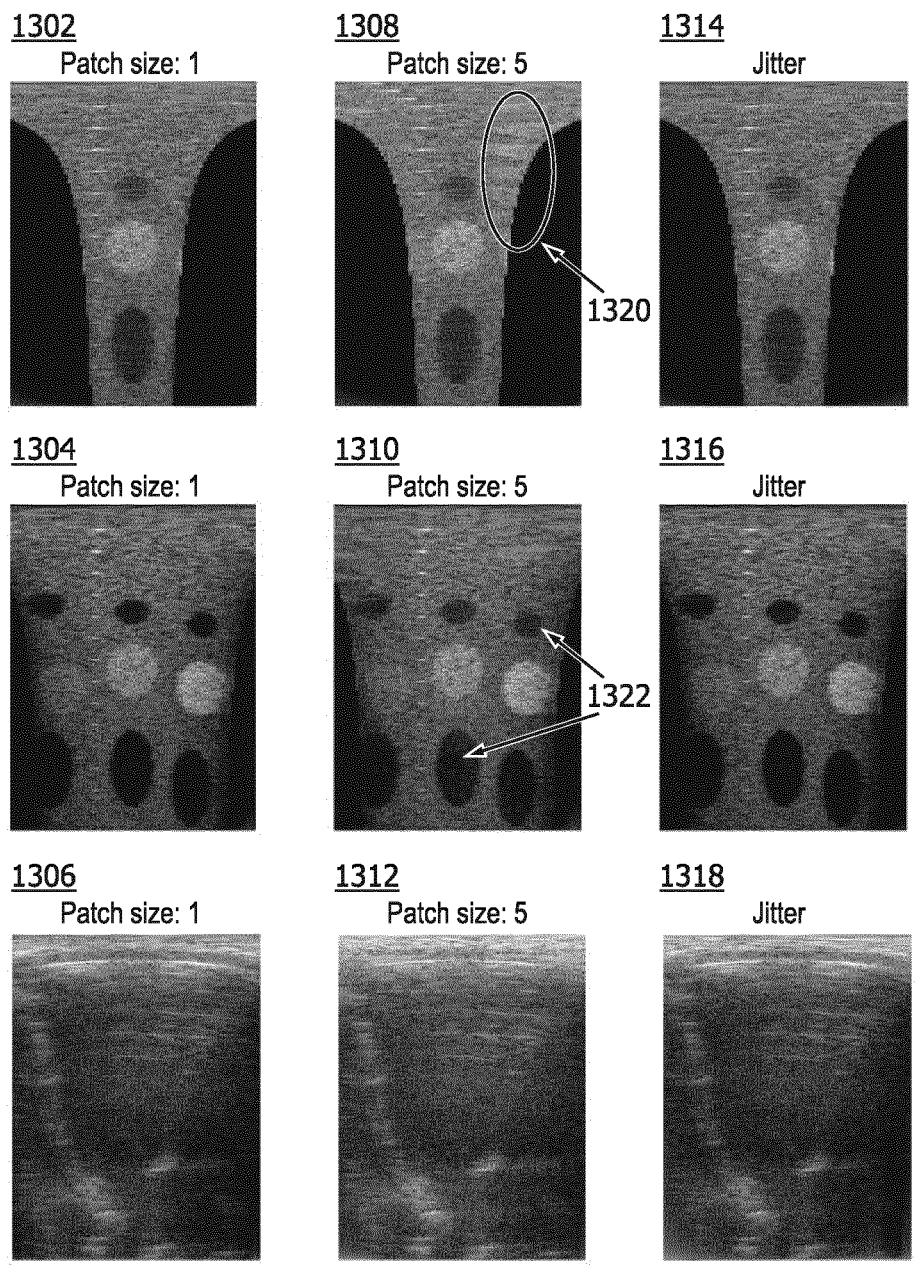

FIGS. 11-13 show examples of original signals and reconstructed signals generated in accordance with the examples of the present disclosure.

In FIG. 11 a simulated per-channel data from S5-1 phased array is shown. Pane 1102 shows the original "truth image," pane 1104 shows the reconstruction generated after encoding the truth image with the jitter sample scheme and decoding the jitter signal generated by the jitter sample scheme, and pane 1106 shows the difference between the truth and reconstruction. All panes are shown with the same dynamic range. This dataset was obtained by simulating a synthetic phantom with various grey levels and point targets, with diverging wave transmissions from a 50 mm virtual apex behind the physical aperture, consisting of 21 angles ranging uniformly from −45° to 45°. The covariance matrix used to calculate the reconstruction was calculated using the data obtained at 0° transmit. Jitter sampling and reconstruction was performed on the data obtained at 8° transmit. Truth and reconstruction data match each other well and the difference data has some content corresponding to the high amplitude and high frequency echoes only.

FIG. 12 shows simulated channel data from a hypothetical 2D transducer array with 4096 elements (64×64). However, for simplicity, instead of displaying raw data for all the channels, one slice of the 2D array is shown. The x-element index is fixed to channel 23 and signals from all y-elements are shown. The full aperture is divided into 16-element-by-16-element subarrays and jitter sampling technique described herein is applied on each subarray. Similar to FIG. 11, true data is presented in pane 1202, reconstruction following the compression with jitter sampling scheme is presented in pane 1204, and the difference is shown in pane 1206. This dataset was obtained by simulating a synthetic speckle phantom with a hyper echoic target in the middle, with a plane wave transmission. Truth and reconstruction data images in FIG. 12 look similar, however the difference image has a lot more content with relatively large amplitude. Although the reconstructed data does not appear as clean as the reconstruction shown in FIG. 11, the down-sampling rate is significantly higher in the 2D case (20% for the 1D array in FIG. 11 versus 6.25% for the 2D array in FIG. 13). Despite the significant down-sampling, the reconstruction scheme is able to recover most of the original data as shown in FIG. 12.

FIG. 13 shows images acquired by diverging ultrasound beams in accordance with examples of the present disclosure. The left column (panes 1302, 1304, and 1306) show images acquired by beamforming and displaying B-mode images directly from raw channel signals. That is, the signal from each transducer element was individually processed by a main beamformer with no microbeamforming. The second column (panes 1308, 1310, and 1312) shows images acquired by typical microbeamforming operations with patch size of 5. The third column (panes 1314, 1316, and 1318) show images generated by original signals compressed with the jitter sampling scheme and reconstructed according to principles of the present disclosure. The top row (panes 1302, 1308, and 1314) shows images from a simulated phantom beamformed from one diverging transmit wave. The middle row (panes 1304, 1310, and 1316) shows images from the simulated phantom beamformed from eleven diverging wave transmits (middle row). Both the top row and middle row images were acquired with a 50 mm focus. The bottom row (panes 1306, 1312, and 1318) shows images from an in vivo cardiac dataset generated from 16 diverging wave transmits and a 50 mm focus.

The jitter sample scheme for encoding and decoding the RF data significantly improves the final image compared to conventional microbeamforming as illustrated in FIG. 13. Both improvements in contrast and reduction in grating lobe artifacts obtained with the jitter sampling reconstruction beamforming. For example, the grating lobe artifacts in circle 1320 in pane 1308 do not appear in the reconstructed image of pane 1314. In the eleven transmit case these grating lobe artifacts are not as pronounced as single transmit since they are slightly reduced by angular compounding with other transmits. However, in another example of the improvements demonstrated by the principles of the present disclosure, the grey level inside the hypo echoic cysts 1322 of pane 1310 are increased and the overall contrast is reduced compared with pane 1316. The grating lobes and reduced contrast artifacts of the microbeamformed images are avoided, and an image much closer to the image beamformed from the per-channel data is obtained using the jitter sampling and reconstruction scheme described herein. For all of the jitter reconstructed images shown in FIG. 13, the covariance matrix was estimated from synthetic data, including the in vivo cardiac data.

Finally in the cardiac example of the bottom row, even the per-channel beamformed image in pane 1306 has some clutter in an area corresponding to the chamber. However with the microbeamformered image in pane 1312, overall image contrast is lower with a lot of clutter introduced due to microbeamforming processing. The cluttering and reduced contrast are not present in the image generated by the jitter sampling and reconstruction scheme in pane 1318.

As described herein, a jitter sampling scheme may be used with a microbeamformer to encode RF data received from transducer elements. The encoded signal may be transmitted to a decoder for reconstruction of the original RF data. The encoding may allow for less data to be transmitted between an ultrasound probe and an imaging system base. The encoding and reconstruction may allow for improved image generation (e.g., via beamforming or other methods) compared to images generated from typical microbeamforming operations. The systems, methods, and apparatuses described herein may allow for the use of unfocused beam imaging (e.g., plane waves, diverging waves) with ultrasound probes that include microbeamformers.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. A system comprising:
   a transducer array including a plurality of transducer elements, wherein the transducer elements are configured to receive ultrasound echoes and convert the ultrasound echoes into electrical signals;
   a microbeamformer coupled to the plurality of transducer elements, the microbeamformer including:
      a first delay line coupled to a first transducer element of the plurality of transducer elements, wherein the first delay line includes a first plurality of memory cells configured to store the electrical signals received from the first transducer element; and
      a second delay line coupled to a second transducer element of the plurality of transducer elements, wherein the second delay line includes a second plurality of memory cells configured to store the electrical signals received from the second transducer element;
      wherein the microbeamformer is configured to jitter sample the electrical signal stored in the first plurality of memory cells and the second plurality of memory cells and generate a jitter signal; and
   a decoder configured to receive the jitter signal and generate a reconstructed signal representative of the electrical signals.

2. The system of claim 1, further comprising a main beamformer configured to generated a beamformed signal based at least in part on the reconstructed signal.

3. The system of claim 1, wherein the microbeamformer is configured to generate the jitter signal by pseudo-randomly summing the electrical signals sampled from the first plurality of memory cells and the second plurality of memory cells.

4. The system of claim 1, wherein the decoder is configured to apply a covariance matrix to the jitter signal to generate the reconstructed signal, wherein the covariance matrix is based, at least in part, on the jitter sample of the electrical signal stored in the first and second pluralities of memory cells.

5. The system of claim 1, wherein the microbeamformer is configured to jitter sample the electrical signal stored in the first and second pluralities of memory cells using a pseudo-random pattern of time sample segments.

6. The system of claim 5, wherein the pseudo-random pattern of time sample segments is configured such that individual memory cells of the first plurality of memory cells and the second plurality of memory cells are sampled no more than once per memory cycle.

7. The system of claim 1, wherein the first delay line is a programmable delay line.

8. The system of claim 1, wherein a first subset of the plurality of transducer elements are grouped into a first patch including the first transducer element and a second subset of the plurality of transducer elements are grouped into a second patch including the second transducer element.

9. The system of claim 1, wherein the first plurality of memory cells are configured as a circular buffer.

10. The system of claim 1, further comprising a main beamformer, which includes the decoder.

11. The system of claim 1, further comprising a transmit controller, wherein the transmit controller provides delays to be added to the jitter signal by the microbeamformer to focus or steer a beam associated with the ultrasound echoes.

12. A method comprising:
acquiring a plurality of samples of an electrical signal, wherein the electrical signal is associated with an acoustic signal;
storing the plurality of samples in a plurality of memory cells, wherein individual memory cells of the plurality of memory cells store individual samples of the plurality of samples;
pseudo-randomly selecting a subset of the plurality of memory cells, wherein the subset includes fewer than the plurality of memory cells;
summing the individual samples of the plurality of samples stored in the subset of the plurality of memory cells to generate a jitter signal; and
decoding the jitter signal to generate a reconstructed signal.

13. The method of claim 12, wherein pseudo-randomly selecting the subset of the plurality of memory cells down-samples the electrical signal.

14. The method of claim 12, wherein decoding comprises applying a covariance matrix to the jitter signal, wherein the covariance matrix is based at least in part on pseudo-randomly selecting the subset of the plurality of memory cells.

15. The method of claim 12, further comprising:
transmitting an ultrasound signal with a transducer array comprising a plurality of transducer elements;
receiving, with the transducer array, the acoustic signal responsive to the ultrasound signal; and
generating, with the plurality of transducer elements, the electrical signal responsive to the acoustic signal, wherein at least one of the plurality of memory cells is coupled to individual ones of the plurality of transducer elements.

16. The method of claim 15, wherein the plurality of transducer elements are grouped into a plurality of patches and summing the individual samples of the plurality of samples comprises summing individual samples associated with at least two of the plurality of patches.

17. The method of claim 15, wherein the ultrasound signal is a plane wave or a diverging wave.

18. The method of claim 12, wherein acquiring the plurality of samples of the electrical signal is controlled by a clock signal.

19. The method of claim 18, wherein a frequency of the clock signal is higher than a Nyquist rate of the electrical signal.

20. The method of claim 12, further comprising adding delays to the subset of the plurality of memory cells, wherein the delays focus or steer a beam associated with the acoustic signal.

* * * * *